United States Patent [19]

Johansson et al.

[11] Patent Number: 5,320,462
[45] Date of Patent: Jun. 14, 1994

[54] METHOD OF PRODUCING DENTAL RESTORATIONS AND MEDICAL PROSTHESES

[75] Inventors: Gunnar Johansson, Onsdagsvägen 23, S-902 66 Umeå; Göran Sjögren, Flintvägen 6, S-902 42 Umeå; Anders Sundh, Kuratorvägen 10, S-907 36 Umeå, all of Sweden

[73] Assignees: Maud Bergman; Gunnar Johansson; Goran Sjogren; Anders Sundh, all of Umea, Sweden

[21] Appl. No.: 834,564
[22] PCT Filed: Aug. 17, 1990
[86] PCT No.: PCT/SE90/00534
 § 371 Date: Apr. 8, 1992
 § 102(e) Date: Apr. 8, 1992
[87] PCT Pub. No.: WO91/02496
 PCT Pub. Date: Mar. 7, 1991

[30] Foreign Application Priority Data

Aug. 17, 1989 [SE] Sweden .................... 89027650

[51] Int. Cl.⁵ .................. B23C 1/00; B01B 11/24; A61K 6/06
[52] U.S. Cl. .................... 409/84; 409/131; 356/376; 433/223
[58] Field of Search .............. 409/84, 80, 79, 293, 409/244, 131; 51/165.71, 165.72; 433/223; 356/376; 364/474.05, 474.26, 474.29

[56] References Cited

U.S. PATENT DOCUMENTS

| | | | |
|---|---|---|---|
| 4,182,312 | 1/1980 | Mushabac | 433/66 |
| 4,478,580 | 10/1984 | Barrut | 433/223 |
| 4,575,805 | 3/1986 | Moermann et al. | 29/160.6 X |
| 4,611,288 | 9/1986 | Duret et al. | 433/213 |
| 4,837,732 | 6/1989 | Brandestini et al. | 356/376 X |
| 4,952,149 | 8/1990 | Duret et al. | 433/215 |
| 5,115,307 | 5/1992 | Cooper et al. | 433/29 |
| 5,131,844 | 7/1992 | Marinaccio et al. | 433/72 |

FOREIGN PATENT DOCUMENTS

| | | | |
|---|---|---|---|
| 54785 | 6/1982 | European Pat. Off. | |
| 311214 | 4/1989 | European Pat. Off. | 433/223 |
| 2936847 | 3/1981 | Fed. Rep. of Germany | 409/84 |
| 9115163 | 10/1991 | World Int. Prop. O. | 433/223 |

*Primary Examiner*—William Briggs
*Attorney, Agent, or Firm*—Cushman, Darby & Cushman

[57] ABSTRACT

This invention relates to a method of producing restorations, prosthesis or the like within dentistry and medical service, a measuring device, a computer and a shaping machine being utilized. According to the invention the method is characterized by the combination of the following moments: a measuring probe (3) provided with at least two lighting points (5-7) and being an integral part of a measuring device provided with at least two cameras (1, 2) is conveyed along the treatment area at the same time as the movements of the measuring probe (3) are registered by means of the cameras (1, 2); data from the cameras are collected by and stored in a computer which is specially programmed for this field of use and which on basis of incoming data can determine the form of the treatment area; the data information stored in the computer is utilized for controlling a shaping machine which out of a working piece shapes a suitable restoration or prosthesis.

2 Claims, 1 Drawing Sheet

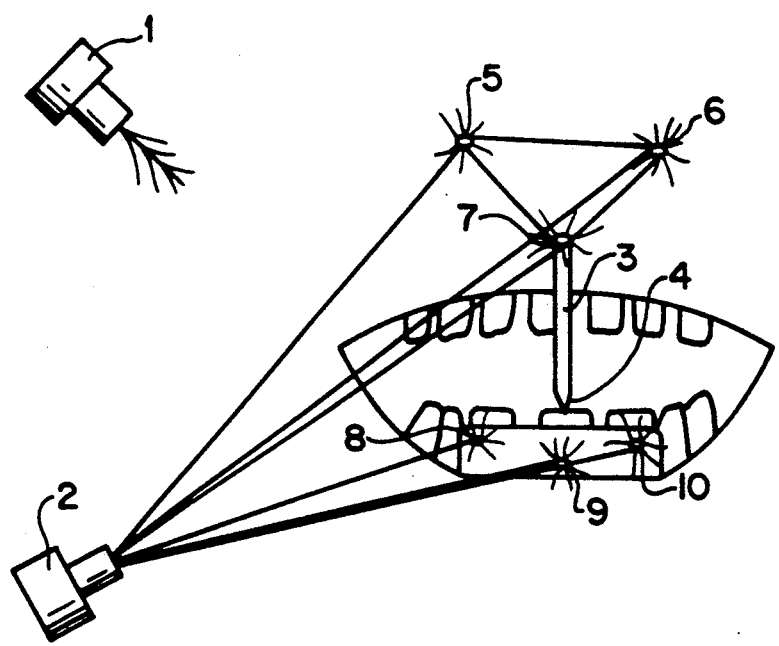

METHOD OF PRODUCING DENTAL RESTORATIONS AND MEDICAL PROSTHESES

BACKGROUND OF THE INVENTION

This invention relates to a method of producing restorations, prosthesis or the like within dentistry and medical service, a measuring device, a computer and a shaping machine being utilized.

According to common technique within dentistry when repairing the teeth the dentist after having drilled the tooth that shall be filled makes an impression of the tooth. Thereafter a model of the tooth is made in plaster, which is utilized by a dental technician as a model when waxing and moulding the restoration. This method is very troublesome and time-consuming and creates many sources of errors. Therefore, new methods of producing restorations and dentures within dentistry have lately began to be developed.

According to a method described in European Patent No. 0 054 785 there is previously known to make an optical reading of the form of the cavity of the tooth. This information is transmitted to a computer, a manual completion of the information being made. The computer controls a milling-machine which shapes a material, whereby a restoration is produced with a form which is similar to the form of the cavity. According to another method which is described in the U.S. Pat. No. 4,182,312 there is previously known to convey a probe around in the cavity of the tooth, the form of the cavity being detected. The information from the probe is transmitted to a shaping machine in a mechanical way, which prepares a restoration with a form which is similar to that of the cavity. None of these two methods, however, gives a satisfactory result but additional working is required.

SUMMARY OF THE INVENTION

This invention relates to a method that shall produce restorations, prosthesis or the like, which have better fit than restorations and prosthesis produced according to known methods. This has been made possible by the method according to the kind mentioned by way of introduction, which is characterized by the combination of the following moments:

A measuring probe provided with at least two lighting points and being an integral part of a measuring device provided with at least two cameras is conveyed along the treatment area at the same time as the movements of the measuring probe are registered by means of the cameras;

Data from the cameras are collected by and stored in a computer which is specially programmed for this field of use and which on basis on incoming data can determine the form of the treatment area;

The data information stored in the computer is utilized for controlling a shaping machine which out of a working piece shapes a suitable restoration or prosthesis.

An essential advantage with this new method is that the form of the treatment area can be determined even if this one is not visually available. According to the new method every separate measuring point in the space becomes evidently defined regarding xyz-coordinates. These measuring data are stored in the computer and can then be the base when shaping the working piece in the shaping machine.

BRIEF DESCRIPTION OF THE DRAWING

In the Drawing

The FIGURE is a schematic view of a device embodying principles of the present invention.

DETAILED DESCRIPTION

A preferred embodiment of a device for measuring the form of a treatment area inside the mouth of a person for instance shall be described more closely with reference to the accompanying drawing. This device is very suitable to use for measuring the form of holes for instance in the teeth made by means of drilling. In that connection the device measures and calculates the internal contour of the cavity of the tooth.

The device comprises two cameras 1, 2, which is suitably of CCD-type. These cameras are intended to register the position of light emitting diodes from different directions and accordingly function as transmitters and/or receivers. The cameras are intended to cooperate with a measuring probe 3 having a point 4. This point is intended to be conveyed along the surface of the cavity for instance. The measuring probe 3 further comprises three lighting points 5–7, which can be active in the form of light emitting diodes or passive in the form of reflectors. The characterizing thing for the light emitting diodes is that they suitably emit IR-light while the reflectors reflect IR-light. The point 4 of the measuring probe 3 has known coordinates (x,y,z) in relation to the three lighting points. Due to that fact the coordinates in the space of the three lighting points can be registered by means of the two cameras which have stationary positions. Of course, the number of cameras can be more than two but if the number of lighting points of the measuring probe is three, it is sufficient with two cameras. If instead three cameras are utilized, it is sufficient to have two lighting points on the measuring probe.

This described measuring device is connected to a computer, whereby data from the cameras can be fed into the computer which is programmed for this special field of use. When the point 4 of the measuring probe 3 is accordingly conveyed along for instance the surface of the cavity, the coordinates in the space of the three lighting points can be exactly determined for different positions, the surface and the form of the cavity being able to be determined by means of the computer.

In order to determine the form of the cavity of the jaw for instance in a more secure way when the patient moves his head it is suitable to arrange three lighting points 8–10 as reference points in the upper jaw or the lower jaw of the patient. If instead three cameras are utilized, it is sufficient to have two lighting points as reference points in the upper jaw or the lower jaw.

Data about the form of the measured cavity which have been collected by and stored in the computer can now be used for controlling a shaping machine, for instance a milling-machine, which out of a working piece shall produce a restoration or the like with the same form of that of the cavity, which restoration is fastened into the cavity of the drilled tooth by the dentist in a suitable way. Thus, with this method it is possible to achieve a very great accuracy when making treatments within dentistry and medical service.

When describing the device the cavity of a tooth in which there has been made a hole by means of drilling has been mentioned as a treatment area. Of course, other treatment areas may be possible, for instance the upper jaw and/or the lower jaw when inserting dentures. An example of a utilization area of the new method within the medical service is the production of artificial limbs for mutilated arms and/or legs.

I claim:

1. A method of producing a dental or medical restoration or prosthesis, comprising:

conveying a measuring probe provided with two lighting points and being an integral part of a measuring device provided with three cameras along a treatment area while registering movements of the measuring probe using the cameras;

collecting data from the cameras by and storing the collected data in a computer which is specially programmed for the field of use of preparing dental or medical restorations or prosthesis and which on the basis of incoming data can determine the form of said treatment area; and utilizing the data thereby stored in the computer for controlling a shaping machine which, out of a working piece, shapes a suitable restoration or prosthesis which fits said treatment area.

2. A method of producing a dental or medical restoration or prosthesis, comprising:

conveying a measuring probe provided with three lighting points and being an integral part of a measuring device provided with two cameras along a treatment area while registering movements of the measuring probe using the cameras;

collecting data from the cameras by and storing the collected data in a computer which is specially programmed for the field of use of preparing dental or medical restorations or prosthesis and which, on the basis of incoming data, can determine the form of said treatment area; and utilizing the data thereby stored in the computer for controlling a shaping machine which, out of a working piece, shapes a suitable restoration or prosthesis which fits said treatment area.

* * * * *